US008481519B2

(12) United States Patent
Hoffmann et al.

(10) Patent No.: US 8,481,519 B2
(45) Date of Patent: Jul. 9, 2013

(54) ISOLATION OF ATRARIC ACID, SYNTHESIS OF ATRARIC ACID DERIVATIVES, AND USE OF ATRARIC ACID AND THE DERIVATIVES THEREOF FOR THE TREATMENT OF BENIGN PROSTATIC HYPERPLASIA, PROSTATE CARCINOMA AND SPINOBULBAR MUSCULAR ATROPHY

(75) Inventors: Hans-Rainer Hoffmann, Neuwied (DE); Rudolf Matusch, Marburg (DE); Aria Baniahmad, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 517 days.

(21) Appl. No.: 11/883,610

(22) PCT Filed: Jan. 28, 2006

(86) PCT No.: PCT/EP2006/000749
§ 371 (c)(1),
(2), (4) Date: Dec. 31, 2008

(87) PCT Pub. No.: WO2006/081997
PCT Pub. Date: Aug. 10, 2006

(65) Prior Publication Data
US 2009/0143466 A1 Jun. 4, 2009

(30) Foreign Application Priority Data
Feb. 5, 2005 (DE) .......................... 10 2005 005 399

(51) Int. Cl.
*A01N 43/00* (2006.01)
*A61K 31/33* (2006.01)

(52) U.S. Cl.
USPC .............................. 514/183; 514/544; 560/61

(58) Field of Classification Search
None
See application file for complete search history.

(56) References Cited

U.S. PATENT DOCUMENTS

| 3,856,946 A | 12/1974 | Debat |
| 4,420,629 A | 12/1983 | Schmidt |
| 5,153,342 A | 10/1992 | DeBella |
| 6,482,447 B2 * | 11/2002 | Revel ........................... 424/727 |
| 2004/0198815 A1 | 10/2004 | Khanuja et al. |

FOREIGN PATENT DOCUMENTS
GB      1177645      1/1979

OTHER PUBLICATIONS

Sonja et al, "Activity-guided isolation of an antiandrogenic compound of *Pygeum africanum*", Planta Med, vol. 72, 2006, pp. 547-551.*
Charles et al "Androgen Resistance, Part 2", Feb. 2003 v 6.1.*
Ishani, et al.; "*Pygeum africanum* for the Treatment of Patients with Benign Prostatic Hyperplasia: A Systematic Review and Quantitative Meta-Analysis;" *The American Journal of Medicine*; vol. 109, No. 8 (2000), pp. 654-664.
Solano, R.M., et al.; "Effects of *Pygeum africanum* extract (Tadenan) on vasoactive intestinal peptide receptors, G proteins, and adenylyl cyclase in rat ventral prostate;" *US National Library of Medicine*; Nov. 1, 2000; vol. 45, No. 3, pp. 245-252.
Sun, Handong, et al.; "Chemical constituents of four medicinal lichens;" *Chemical Abstracts Service*; (1990).
Yakugaku Zashi & Fujikawa; "Beilstein Institut zur Forderung der Chemischen Wissenschaften;" Frankfurt am Main, Germany; vol. 60, 1940, pp. 473, 477.
Yakugaku Zashi & Fujikawa; "Beilstein Institut zur Forderung der Chemischen Wissenschaften;" Frankfurt am Main, Germany; vol. 56, 1936, pp. 237, 245.
Herzig, et al.; "Beilstein Institut zur Forderung der Chemischen Wissenschaften;" Frankfurt am Main, Germany; Monatsh. Chem. 24, 1903, p. 908.
Stephenson & Robertson; "Beilstein Institut zur Forderung der Chemischen Wissenschaften;" Frankfurt am Main, Germany; J. Chem. Soc., 1930, pp. 313, 318.
Strong, K.M.; "African Plum and Benign Prostatic Hypertrophy;" *Journal of Herbal Pharmacotherapy*; vol. 4, No. 1 (2004), pp. 41-46.
Schleich, Sonja; "Nichtsteroidale Antiandrogene naturlichen Ursprungs zur Behandlung des Prostatakarzinoms;" http://archiv.ub.uni-marburg.de/diss/z2005/0223/pdf/dss.pdf>.
De Jesus, et al.; "*Metabolites of Aspergillus ustus Part 4*;" J. Chem. Soc. Perkin. Trans. I (1987), p. 2253-57.

* cited by examiner

*Primary Examiner* — Brandon Fetterolf
*Assistant Examiner* — Jean Cornet
(74) *Attorney, Agent, or Firm* — D. Peter Hochberg; Sean F. Mellino

(57) ABSTRACT

A method for isolating atraric acid from biological material, atraric acid derivatives, the chemical synthesis thereof, and the use of atraric acid and the derivatives thereof for treating or producing a medicament for treating benign prostate hyperplasia, prostate carcinoma or spinobulbar muscular atrophy is provided. In addition, a basic substance for the development of other agents used for treating benign prostate hyperplasia, prostate carcinoma, or spinobulbar muscular atrophy is provided.

12 Claims, 9 Drawing Sheets

ISOLATION OF ATRARIC ACID, SYNTHESIS OF ATRARIC ACID DERIVATIVES, AND USE OF ATRARIC ACID AND THE DERIVATIVES THEREOF FOR THE TREATMENT OF BENIGN PROSTATIC HYPERPLASIA, PROSTATE CARCINOMA AND SPINOBULBAR MUSCULAR ATROPHY

CROSS-REFERENCE TO RELATED APPLICATIONS

This application is a National Stage application of International Application No. PCT/EP2006/000749, filed on Jan. 28, 2006, which claims priority of German application number 10 2005 005 399.8, filed on Feb. 5, 2005.

BACKGROUND OF THE INVENTION

1. Field of the Invention

The present invention relates to the isolation of atraric acid from biological material, to atraric acid derivatives, to the chemical synthesis thereof, as well as to the use of atraric acid and of the derivatives thereof for the treatment or the production of a medicament for treating benign prostate hyperplasia and/or prostate carcinoma, particularly therapy-resistant prostate carcinoma, as well as spinobulbar muscular atrophy. The present invention furthermore relates to the use of atraric acid and its derivatives as the lead substance in the development of new active substances for the treatment or the production of a medicament used for treating benign prostatic hyperplasia and/or prostate carcinoma, particularly therapy-resistant prostate carcinoma, as well as spinobulbar muscular atrophy.

2. Description of the Prior Art

Benign prostatic hyperplasia (BPH) is a benign enlargement of the glandular epithelium, of the connective tissue and of the smooth muscles in the transitional zone of the prostate. BPH afflicts 50% of men over 60 years of age, in men over 75 years of age the percentage is even 75%. Thus, BPH is responsible for the most frequent form of bladder dysfunction in men.

The symptoms of BPH comprise obstructive and irritative complaints. The obstructive symptoms include diminished urinary stream, prolonged micturition time, dribbling and residual urine, while the irritative symptoms are manifested in increased micturition frequency, painful micturition, and urge incontinence. Regarding the etiology of BPH, there are various hypotheses currently being discussed.

Prostate carcinoma is the most common cancer affecting men in the Western countries and represents the second most common cause of cancer death after lung cancer. Although, in its etiology, the prostate carcinoma is not directly connected to BPH, patients suffering from a severe form of BPH show gene anomalies that are very similar to those of prostate cancer patients. While BPH affects above all the transitional zone of the prostate, a carcinoma occurs preferably in the peripheral zone.

The reasons for the development of a prostate carcinoma are various gene defects, which may be due to a predisposition in the family. Thus, various mutations of the androgen receptor occur in the persons suffering from prostate carcinoma. Reduced activity of the 5 α-reductase type II, however, reduces the risk of developing a carcinoma. Furthermore, different tumour suppressor genes, such as Rb gene on chromosome 13 q, can be affected by mutations and can thus become inactivated. On the other hand, a hyperfunction of oncogenes contributes to tumour formation. In addition, a significant role is played by methylations of important growth-regulating and detoxifying genes, the genes thereby becoming unable to function and clearing the way for cancer. According to the most recent state of science, a big contribution is made by inflammation processes from which emanate preneoplastic or neoplastic lesions.

The initial therapy for treating prostate carcinoma usually consists in removing the prostate by radical prostatectomy, or in irradiation to remove the degenerated cells. An advanced, metastasising prostate carcinoma can be treated by a palliative hormone therapy. The total androgen blockade, which is applied nowadays, includes the combination of operative and chemical castration. The purely antiandrogenic agents bicalutamide (CASODEX®), flutamide (FUGEREL®) and nilutamide (ANANDRON®) act selectively on the androgen receptors of the target organs while cyproterone acetate (ANDROCUR®) also occupies progesterone receptors and glucocorticoid receptors. However, hormone therapy cannot heal advanced prostate cancer. The treatment initially causes an antiandrogen-dependent inhibition of tumour growth. However, after two years, on average, resistance to the therapy occurs. First, a hyperexpression of various coactivators enables the activation of the androgen receptor through non-androgenic steroids. Later on, even antiandrogens, such as the active flutamide metabolite, 2-hydroxyflutamide, are able to activate the androgen receptor, and the tumour becomes independent of androgens.

SUMMARY OF THE PRESENT INVENTION

The object of the present invention was thus to find new active substances for treating BPH and/or prostate carcinoma, particularly such active substances which also inhibit the growth of androgen-independent prostate cancer cells.

Spinobulbar muscular atrophy (SBMA) is a neurodegenerative disease or a hereditary neurogenic muscle disorder which is connected with muscular atrophy and which afflicts only men. The death of the peripheral motoneurons (spinal anterior horn cells), which are located in the spinal cord and whose processes extend to the muscles, leads to muscular atrophy, muscular asthenia (pareses), involuntary muscle twitching (fasciculations), as well as trembling (tremor). Muscular asthenia initially affects the proximal regions (upper arms, thighs). If the motoneurons which are located in the brain stem (bulbus), that is, the nerve cells in the cerebral cortex and their connections to the spinal cord, are affected, the speech muscles, masticatory muscles and swallowing muscles are weakened, too. In addition, the disorder of the central motor system leads to an increase in muscle tone (spastic paralysis).

The genetic cause of spinobulbar muscular atrophy is thought to be an increase in the number of CAG base triplets in exon 1 of the androgen receptor gene which is located on the sex-determining X chromosome. This leads to an expansion of the polyglutamine region in the androgen receptor. The thus pathologically altered androgen receptors accumulate over a prolonged period of time, form inclusions in the cell nucleus, and are likely to lead to the death of the neurons.

The ligand-dependent accumulation of pathologically altered androgen receptors in the cell nucleus is made responsible for the pathogenesis of spinobulbar muscular atrophy.

Transgenic mice that had a human androgen receptor gene with an increased number of CAG base triplets, revealed neuromotor impairments that were particularly distinct in male experimental animals. The impairments of these rats that were similar to SBMA could be alleviated by castration or aggravated by administration of testosterone. These experimental results lead to the assumption that inactivation of the androgen receptor in SBMA patients can alleviate the progress of the disease. The significance of their ligand bond for the aggregation of androgen receptors was also examined with the aid of androgens and androgen antagonists. Stimulation with testosterone of cells that expressed a pathologically altered androgen receptor led to characteristic inclusions in the cytoplasm. By contrast, only a small number of inclusions were observed when treating these cells with the partial androgen antagonist cyproterone, and no inclusions when they were treated with flutamide. These observations support the hypothesis that androgen antagonists are able to prevent the formation of androgen receptor aggregates. However, to date, there is no proof that the formation of androgen receptor aggregates is responsible for the progress of spinobulbar muscular atrophy.

Another object of the present invention was thus to find new active substances for the treatment of spinobulbar muscular atrophy.

The objects of the present invention were achieved by isolating substances having antiandrogenic activity from the bark of the African plum tree *P. africana*.

Surprisingly, the substance atraric acid was isolated from the bark of *P. africana* or from lichens growing on the bark of *P. africana*, and it was found that this substance had high antiandrogenic activity. Atraric acid is even able to inhibit the growth of prostate cancer cells that do not respond to a treatment with hydroxyflutamide.

In addition, it could be proved that atraric acid has an agonistic effect on the two estrogen receptors (estrogen receptor alpha (ERα) and estrogen receptor beta (ERβ)).

Apart from α adrenoreceptor blockers, such as doxazosin (CARDURA®), and 5 α reductase inhibitors, such as finasteride (PROPECIA®), there are numerous phytopharmaceuticals commercially available for the drug treatment of BPH. The preparation TADENAN® of the company Debat contains a chloroform extract from the bark of *Prunus africana* (Hook. f.) Kalkm. (*Pygeum africana*). It has already been approved in France for the treatment of benign prostatic hyperplasia since 1969 and has meanwhile become widespread in Italy and the USA as well. In Germany, however, this chloroform extract has not been approved. In that country, extracts and preparations from the fruits of the American saw palmetto (*Sabal serrulata*=*Serenoa repens*, PERMIXON®), from the root of the stinging mettle (*Urtica dioica*), from pumpkin seeds (*Cucurbita pepo*), from rye pollen (*Secale cereale*) and from the root of the African lily (*Hypoxis rooperi*) have been approved for the treatment of BPH.

*Prunus africana* (Hook. f.) Kalkm., having the obsolete botanical taxonomic name *Pygeum africana* (Hook. f.), is a member of the subfamily of the Prunoideae within the Rosaceae. The Prunoideae include woody plants with stone fruits. The genus of *Prunus* is the most comprehensive genus in this subfamily. It includes, for example, the cherry (*Prunus avium* L.), the peach (*Prunus persica* L.), the plum (*Prunus domestica* L.) and the almond (*Prunus dulcis* (Mill.) D. A. Webb). The African plum tree, *Prunus africana* (Hook. f.) Kalkm., is the only species of this genus that is found on the African continent and should therefore differ from the other members of the same subfamily in terms of its components.

The object of the present study was to isolate the antiandrogenically active natural substances from the bark of *Prunus africana* since an extract containing a large number of components can be standardised only when all the active substances, including their exact strength of action, are known, and because such an extract causes greater stress to the organism. A further object was to produce new antiandrogenic active substances on the basis of the antiandrogenically active substances isolated from *P. africana*.

DETAILED DESCRIPTION OF THE PRESENT INVENTION

Figure 1:
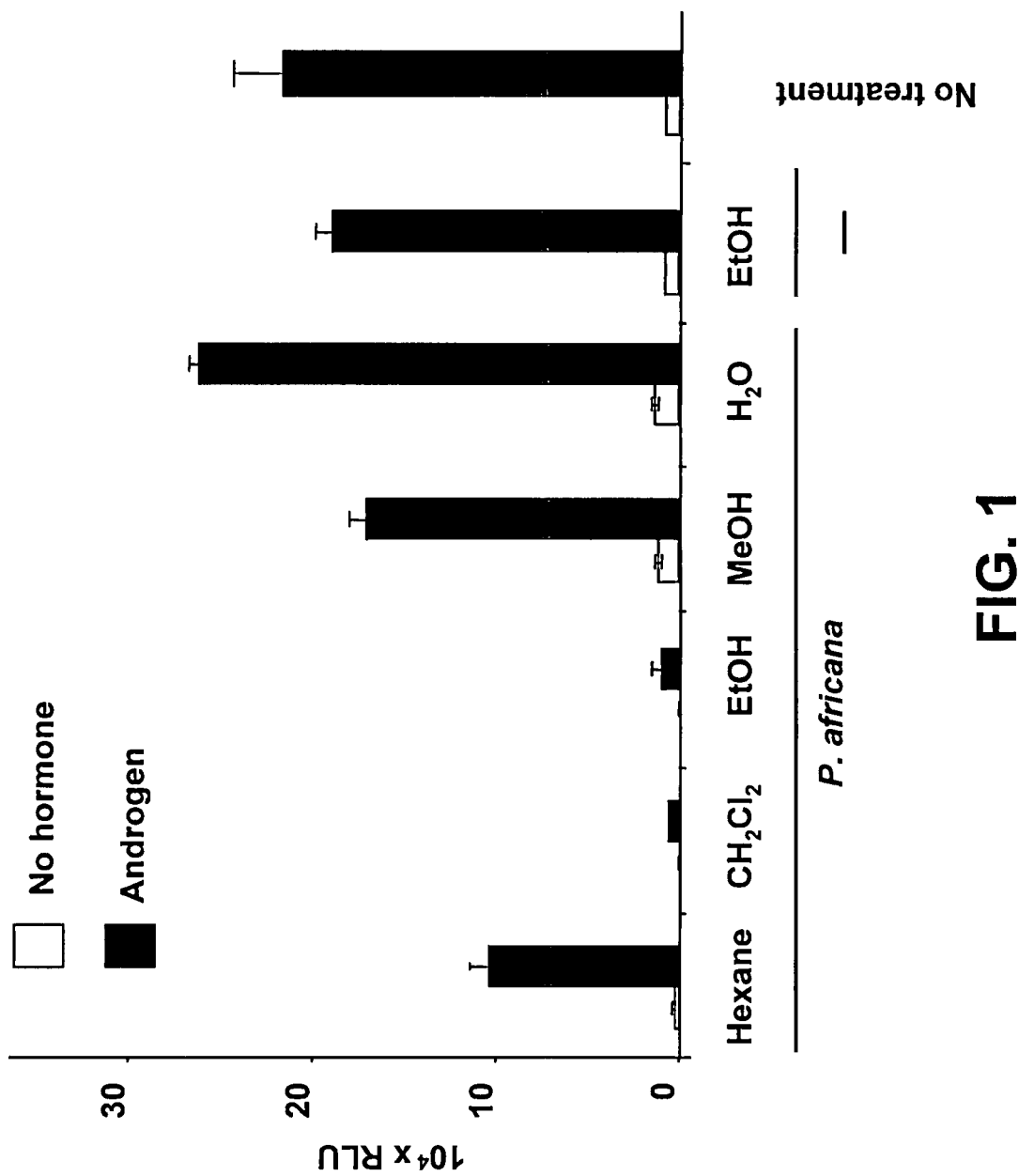
FIG. 1 shows the inhibition of the activity of an androgen in the luciferase assay by different extracts from *P. africana*.

First, the antiandrogenic efficacy of different *Pygeum* extracts was compared. The active compounds were then isolated by activity-guided fractionation. For selective fractionation of the bark material of *P. africana* (Hook. f.) Kalkm., selective extracts were first prepared.

Generally, the components of plant drugs are characterized by a high degree of biodiversity which is reflected in a large number of the most varied compounds. To nevertheless obtain extracts having a manageable number of components, it has proven useful to perform a prefractionation according to solubility in solvents of increasing polarity. Because of the restriction in the range of polarity and the enrichment of substances of lower concentrations, the resulting selective extracts are easier to handle chromatographically and thus, following further fractionation, ultimately enable the isolation of active components.

In the present study, the procedure of selective extraction was performed twice. The plant material, which had been reduced to small pieces, was sieved, subsequently further reduced in size in n-hexane, using an ULTRA-TURRAX® machine, and finally filled in a stainless steel cartridge (40×10 cm and 80×10 cm), closed on both sides with steel frits. By an HPLC pump, the solvents were passed through the filled cartridge according to increasing polarity (n-hexane, dichloromethane, methanol, methanol/water (50/50) and water). This extraction was in each case performed to exhaustion, and the extracts obtained were then, under reduced pressure, narrowed down to dryness. This extraction method is extremely mild, so that temperature, stress and direct action of oxygen and light on the drug are prevented. What is essential, however, is that the components are thereby presorted in extracts ordered according to polarity, and can thus be chromatographed more easily.

Considering the mass proportions of the selective extracts in the total amount of extract, it is clear that the plant material predominantly contains methanol-soluble components. The amounts of the lipophile extracts from n-hexane and dichloromethane were less significant. Generally, there are resins, oils, fats or fat-like substances contained in the hexane extract. The long-chain alcohols and fatty acids from *P. africana* should therefore be found in that extract. The phytosterols and pentacyclic triterpenes can be assumed to be contained in the dichloromethane extract. Highly polar plant components, such as amino acids, inorganic salts or saccharides, however, are only extracted with methanol/water or water.

Apart from the selective extracts, an ethanolic complete extract from the bark of *P. africana* (Hook. f.) was prepared too. To this end, 300 g of the sieved plant material in absolute ethanol was further reduced in size using an ULTRA-TURRAX® machine, and extracted in several portions with a total of 5 l of ethanol. Then, the extract was filtered and finally narrowed down to dryness under reduced pressure.

The potentially antiandrogenic efficacy of the extracts obtained was examined with the androgen receptor-dependent MMTV-luc reporter gene assay, in the following designated as luciferase assay.

In that assay, the enzyme luciferase serves as a reporter gene. Luciferase is an oxidoreductase from the North American firefly *Photinus pyralis*, which dehydrates the substrate luciferin in the presence of aerial oxygen, ATP and $Mg^{2+}$ ions, to oxyluciferin. The energy emitted in the process is emitted as light.

The reporter gene luciferase is located on the plasmid pMMTV-luc (MMTV=Mouse mammary tumour virus), on which is also located the androgen-responsive element (ARE). The plasmid pMMTV-luc is transfected, together with the androgen receptor expression vector, into fibroblasts of the monkey kidney. If an androgen is added thereto, this androgen will bind, in a complex with the androgen receptor, to the androgen-responsive element. This process then initiates the transcription of the following gene, namely that of the luciferase reporter gene. The amount of the expressed luciferase is directly proportional to the amount of light released when adding luciferin, and the amount of light can be quantified by measuring the emission at $\lambda=562$ nm. If apart from the androgen there is also an antiandrogenic substance or an antiandrogenic extract, the transactivation of the luciferase reporter gene by the androgen-responsive element is inhibited and later, when the substrate is added, a correspondingly smaller amount of light energy is released. Since the decrease in the amount of light is directly proportional to the inhibitory effect of the antiandrogen, this assay is excellently suitable for the search for new antiandrogenic lead structures.

The extracts were then examined at two concentrations (300 μg/ml and 600 μg/ml) for their antiandrogenic bioactivity using the luciferase assay. For evaluation, the antiandrogenic effect was calculated as the percent inhibition against a control wherein only pure solvent had been added. The most effective extract was then to be subjected to a further activity-guided fractionation.

FIG. 1 shows that the selective hexane extract from *P. africana* has a weak antiandrogenic activity, which is presumably due to the high content of free and esterified fatty acids and long-chain alcohols.

The selective dichloromethane extract from *P. africana* revealed the highest antiandrogenic effect in the assay. This extract was therefore selected for the further activity-guided fractionation.

With increasing hydrophilicity of the selective *Pygeum* extracts, the antiandrogenic activity decreases significantly.

The ethanolic complete extract from *P. africana* on the other hand reveals a strong effect. This suggests that with ethanol the same antiandrogenic substances were extracted as in the selective dichloromethane extract. The latter is even more potent since in this extract an enrichment with active substances was successfully accomplished.

In the search for active compounds in a complex mixture of numerous substances, the method of activity-guided fractionation has proved to be useful. To this end, the plant extract is first tested for its bioactivity. When an effect occurs, the sample is separated by chromatography, and all of the fractions are again tested for their activity. As a rule, the activity is not distributed over all fractions, but is found in a small number of clearly defined fractions since in those fractions an accumulation of active substances has taken place. These active fractions are then selected and are further fractionated with another separation method. This procedure is repeated with increasingly specific separation methods until the active substances have finally been isolated. The combination of different separation methods (selective extraction, extraction by shaking out, normal phase chromatography and reversed phase chromatography, etc.) reduces the number of fractionation steps and thereby the time needed. The isolated substances are then identified and quantified using various analytical methods, and finally tested for their efficacy, as individual substance and in mixtures of all active compounds. If there is correspondence between a reference substance and the compound isolated from the extract, the identified substances are considered to be confirmed.

This method was also applied in the present study. First, the extract showing the highest efficacy was selected. This was the selective dichloromethane extract from *P. africana*, which on account of the approach of selective extraction was already prefractionated. The further fractionation of the extract was performed by gradient extrography—a chromatography on normal phase.

The process of extrography was developed for the fractionation of crude oil distillation residues. It serves to separate complex mixtures, the components of which encompass a wide range of polarities. The complex mixture is separated with a coarse stepped gradient into a manageable number of fractions, each fraction having a smaller range of polarity than the one before. This leads to an accumulation of substances of defined polarity in the respective fractions. This method was modified for the separation of plant extracts, particularly by shortening the sample zone to a few centimetres. In this way, it is possible to fractionate large amounts of extracts within a relatively short period of time.

In extrography, the extract is first dissolved in a suitable solvent and is adsorbed on approximately five times the amount of coarse silica gel. To this end, the silica gel is combined with the clear extract solution, this mixture is treated with ultrasound, and thereafter the solvent is removed on the rotary evaporator, with slow turning of the piston, until a dry, flowable material remains. This process results in a presorting of the sample molecules on the silica gel. The extremely polar silanol groups of the silica gel initially adsorb at their surface the sample molecules of the highest polarity. This new surface of polar compounds in turn adsorbs somewhat less polar substances from the extract. This leads to several layers of sample molecules of decreasing polarity in the silica gel pores. Thus, the most apolar substances are located on the new pore surface. It inevitably results therefrom that the amount of the dissolved extract must be placed on the silica gel in a single portion, and not in several portions. Otherwise, with each portion, all the polarities of the substances would again be adsorbed thereon after withdrawal of the solvent. The silica gel with the adsorbed extract is packed into the separating column in front of the chromatographic bed of fine silica gel (Macherey—Nagel Si60, 15-25 μm). If the solvent gradient is then started with a lipophile eluent, initially only the lipophile substances will be dissolved at the surface and will be passed to the chromatographic separation bed. In the course of the gradient, the polarity of the eluent is increased so that now substances of increasing polarity are available to chromatography. Thus, the presorting of the sample molecules on the silica gel enables the fractionation of large amounts of substances. Overloading of the separation bed is prevented since the sample molecules do not enter into the separation bed all at once, but gradually, sorted in groups of different polarity.

The solvent gradient most suitable for the selective dichloromethane extract was determined by a series of pre-trials with different gradients. As in the selective extraction, n-hexane was chosen as the most lipophile solvent component. In the further course of the gradient, dichloromethane should be admixed slowly and evenly since the separation of the extract, which after all was prepared with that solvent, should be most successful with dichloromethane. Subsequently, the admixture of methanol and finally the admixture of water follow within a relatively short period of time since it is hardly to be presumed that compounds of such polarity are to be found in the dichloromethane extract. 0.1% trifluoroacetic acid was added to all of the eluents in order to prevent acid compounds from dissociating.

Extrography was performed twice, on a preparative scale, with the selective dichloromethane extract from *P. africana* (extrography 1=E1 and extrography 2=E2). Upscaling to the large scale required adjustment of the column dimension and the flow rate of the eluent. A stainless steel cartridge (Merck PREPBAR® 40×10 cm) packed with silica gel was used as the column. The packing of this cartridge was compressed with the aid of a pressing tool and a variable column head. The sample zone, consisting of the adsorbed extract, was located in the lower part of the chromatography tube. The eluents were pumped at a flow rate of 120 ml/min, using an HPLC pump, from the bottom to the top, in order to prevent air pockets.

The 35 fractions obtained from the preparative gradient extrography (Table 1) were examined by HPLC analysis for their constituents and were compared with one another and with the unfractionated selective dichloromethane extract. In this process, all the fractions were chromatographed in the same amounts, so that a direct comparison of the concentrations of identical compounds in the individual fractions could be performed on the basis of the UV absorption and thus the surfaces in the chromatogram.

When comparing the chromatograms of the extrography fractions with the chromatographic overview, it can be clearly seen that the extrography was successful in accomplishing the substance separation of the components from one another. Some substances strongly accumulated in the corresponding fractions.

The 35 fractions were subjected to the luciferase assay for testing for antiandrogenic activity. All fractions were tested at the concentrations of 30 μg/ml and 60 μg/ml. Of the 35 fractions, three proved to be extremely effective, namely the neighbouring fractions F6, F7 and F8, as can be seen from FIG. 2.

On comparison of the HPLC chromatograms of the fractions F6, F7 and F8 it was observed that all three fractions have a very similar profile of components. The number of peaks was clearly reduced compared to the unfractionated selective dichloromethane extract. A double peak at a retention time of 39 minutes stood out in particular, since it is not found in any of the other 32 fractions. This fact leads to the assumption that one of the two substances, or even both substances, that are represented by the double peak could be the active component(s) of *P. africana*.

To obtain the antiandrogenic active substances, the last separating stage had to be performed, namely the further isolation from the antiandrogenically active extrography fractions.

Of the three extrography fractions F6, F7 and F8, fraction F8, which was present in a sufficient amount, was selected for further preparative separation. The analytical separation method was shortened and was converted to the preparative scale by adapting the column dimension and the flow rate. After several separations, the substances P3, P5, P7, P9 and P10 could be obtained in an amount sufficient for the luciferase assay.

The isolated substances P3, P5, P7, P9 and P10 were tested for their antiandrogenic action by the luciferase assay. The results are shown in FIG. 3.

Figure 3:
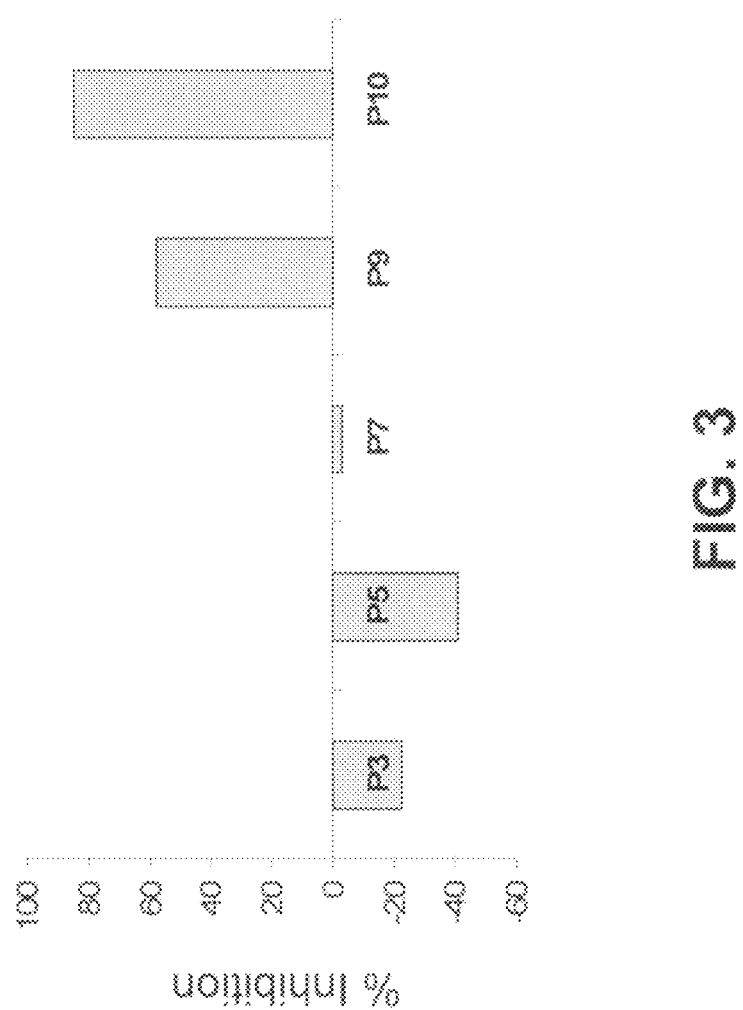
FIG. 3 illustrates the antiandrogenic action of compounds isolated from the fraction F8 of the selective methylene chloride extract.

From FIG. 3 it is clearly apparent that the substances P9 and P10 are the antiandrogenically active compounds from *P. africana*. In the luciferase assay, the compound P5 showed moderate androgenic activity, P3 proved to be weakly androgenic, and with P7 no significant effect could be observed.

Prior to the preparative separation of F8, the fraction was dissolved in the solvent mixture of the chromatography starting conditions (20% acetonitrile (ACN), 80% water). A residue remained which could be filtered off and could also be tested by dissolving it in ethanol/DMSO. The residue revealed no effect in the luciferase assay.

Figure 5:
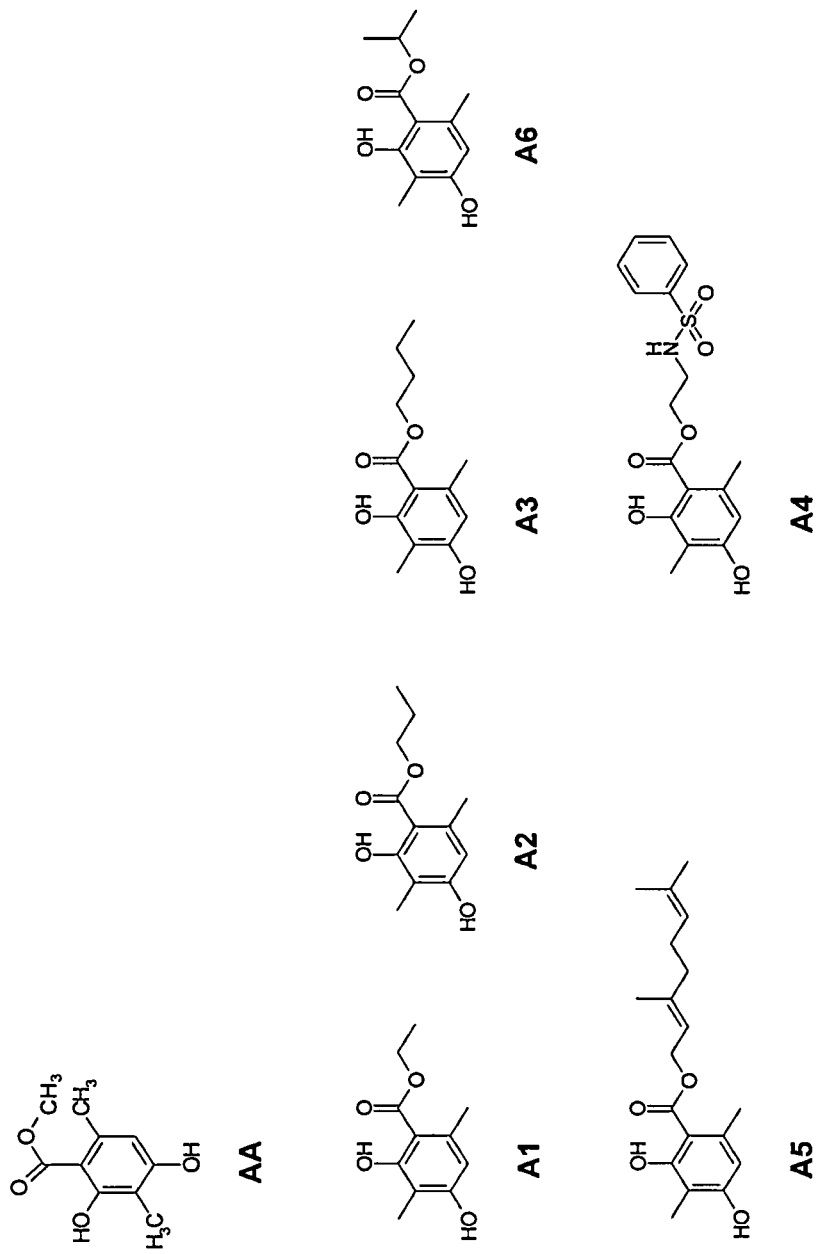
FIG. 5 is a representation of the structural formula of atraric acid (AA) and atraric acid derivatives (A1 to A6).

For clarification of the structure of the substance P9, the images of $^1$H-NMR, $^{13}$C-NMR, UV, IR and EI-MS spectra were used. P9 could be identified as methyl-2,4-dihydroxy-3,6-dimethylbenzoate, also designated as methyl-β-orcinol-carboxylate, with the trivial name of atraric acid. The designation "acid" is somewhat misleading since the carboxylic acid function of atraric acid is not present in its free form, but is esterified with methanol. Nevertheless, atraric acid, on account of the two phenolic hydroxyl groups and the phenylogous carbonyl group, does have acid properties. The structural formula of atraric acid (AA) is shown in FIG. 5.

Atraric acid was isolated as colourless needles from fraction F8. The substance has a characteristic woody smell. Apart from the absorption bands for the methoxycarbonyl group, the IR spectrum of a solution of atraric acid in chloroform shows two bands for the two hydroxyl groups. The OH valence oscillation at $v_{max}$=3040 cm$^{-1}$ suggests the presence of an intramolecular hydrogen bridge formed by the molecule between the hydroxyl group at position C-2 and the carbonyl group. On diluting the solution, the band is maintained at the same position. However, when the sample is diluted the absorption band of the OH valence oscillation at $v_{max}$=3400 cm$^{-1}$ is shifted towards greater wavenumbers, which suggests the presence of an intermolecular hydrogen bridge. The dilution causes the intermolecular hydrogen bridge between the hydroxyl group at C-4 and the carbonyl group of a second molecule to break open, bringing about an increase in the bond strength of the OH group so that a higher energy amount is necessary to excite the valence oscillation.

The intramolecular hydrogen bridge is also visible in the $^1$H-NMR spectrum. The signal of the proton of the hydroxyl group at C-2 which is involved in the intramolecular hydrogen bridge is unusually sharp and is strongly shifted towards the deep field (δ=11.98 ppm). In the case of an HD exchange, this proton will not be replaced by deuterium to the same extent as is the case with the proton of the other hydroxyl group at C-4. This fact shows that the intramolecular hydrogen bridge has to be considerably stronger than the intermolecular bridge. An image of the crystal structure of atraric acid was successfully recorded in 1983.

The $^1$H-NMR spectrum of atraric acid exhibits six singlets. The signals of the methyl groups are located at shifts of $\delta=2.03$ ppm and $\delta=2.39$ ppm. A singlet with the signal intensity of three protons at the shift of $\delta=3.85$ ppm suggests a methoxycarbonyl group, which is confirmed by the signals in the $^{13}$C-NMR spectrum at $\delta=51.8$ ppm and $\delta=172.6$ ppm. The $^{13}$C-NMR spectrum shows an extreme high-field shift of the signal for the methyl group at C-3 at $\delta=7.6$ ppm, which can be explained by the strong electron-attracting effects of the two hydroxyl groups on the neighbouring C atoms. This position of the methyl group could be confirmed by an HMBC experiment (HMBC=Heteronuclear Multiple Bond Correlation), which exhibits in its spectrum a cross signal for the $^3$J(C,H) coupling between the methyl protons at C-3 with C-2 and C-4.

The assignment of all the protons to the corresponding carbon atoms was realised by the recording of an HMQC spectrum (HMQC=Heteronuclear Multiple Quantum Coherence).

The EI mass spectrum of atraric acid yields a molecule ion peak at m/z 196. The empirical formula $C_{10}H_{13}O_4$ could be confirmed by the fine determination of mass. The spectrum also shows the two characteristic fragment ion peaks of atraric acid. The fragment ion at m/z 164 is formed by the separation of methanol, wherein the methyl group of the methoxycarbonyl group forms methanol with the proton of the hydroxyl group at C-2 and is then split off as said methanol. This is characteristic for a methyl salicylate partial structure. A further fragmentation causes the separation of carbon monoxide, so that a second fragment ion peak is formed at m/z 136.

The UV spectrum of atraric acid shows three maxima at $\lambda$ = 217, 245 and 307 nm. Alkaline conditions lead to a yellow colour of the solution and thereby to a bathochrome shift of the maxima in the UV spectrum.

It is possible to recrystallise atraric acid from acetone in order to receive monocline crystals. In addition, due to the salicylate partial structure, atraric acid together with ion (III) chloride solution gives a violet colour. All analytical data are in good accord with the values appearing in the literature.

For quantitative analysis of atraric acid in the selective dichloromethane extract from *P. africana*, a calibration line was established with a reference substance of atraric acid of a purity of more than 99%. This resulted in a content of 0.16% (m/m) of atraric acid in the selective dichloromethane extract.

In the luciferase assay, atraric acid exhibits a clear antiandrogenic activity. The present invention therefore relates to the use of atraric acid for the treatment of benign prostatic hyperplasia and for the production of a medicament for treating benign prostatic hyperplasia.

Atraric acid has already been isolated from the bark material of various higher plants such as *Newbouldia laevis, Alseodaphne andersonii, Acer nikoense, Xylosma velutina* and *Ekebergia pterophylla*.

Atraric acid is, however, also known as a lichen substance. Lichens are epiphytes, i.e. symbiotic organisms consisting of fungi (mycobiont) and algae (photobiont). Atraric acid can be present in lichens in the free form. It also serves as a component of depsides and depsidones. For instance, the well known lichen substance atranorin is a depside of atraric acid and hematommic acid and is synthesized through the polyketide metabolism by various lichen species.

This fact evokes the question of whether atraric acid really is a secondary metabolite of *Prunus africana* (Hook. f.) Kalkm. or if the bark of the tree had been colonized by a lichen producing atraric acid as a polyketide through the pathway of acetate-polymalonate synthesis.

Looking at the bark drug of *Pygeum africana* under the microscope, hyphens are clearly visible, which confirms that a lichen is present. This suggests that atraric acid originates from the polyketide metabolism of the lichen and is not a secondary plant metabolite of *Pygeum africana*.

Atraric acid belongs to the lichen acids, which are polyacetates and whose biogenesis takes place through the fungus component of the plant thallus. Like other lichen acids, atraric acid is considered to be antimicrobial and nematocide as well.

Atraric acid can meanwhile also be produced entirely synthetically from 3-methyl-4-methylene-2-oxetane and acetic acid methyl ester.

Figure 4:
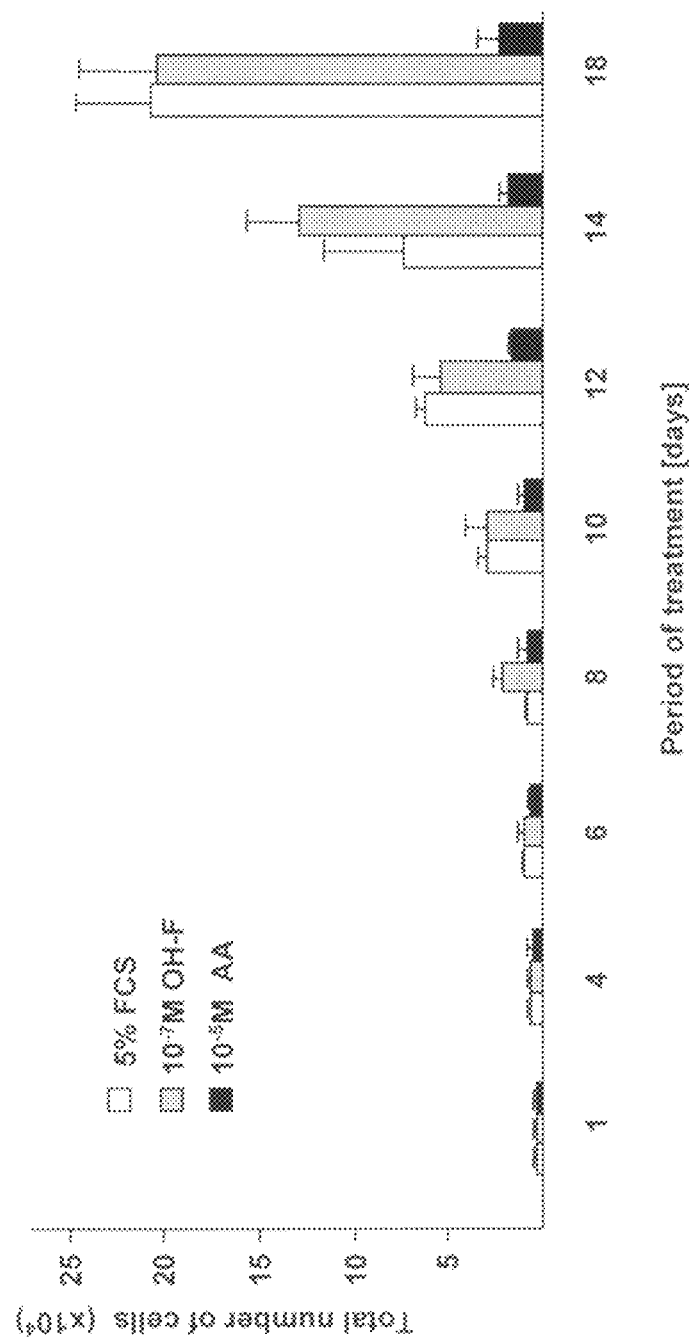
FIG. 4 illustrates the inhibition of the growth of human prostate carcinoma cells by atraric acid.

The growth of prostate cells and prostate cancer cells is originally dependent on androgens. To test whether the androgen antagonism of atraric acid also affects cell growth, the human prostate cancer cell line LNCaP was used, which is known to show androgen-dependent growth. LNCaP cells were cultured in the presence of 10 μM atraric acid. FIG. 4 shows that the cells treated with 10 μM atraric acid already on the 8th day of treatment showed a growth that was clearly slower than that of the untreated cells. This effect was even more prominent by day 18 of the treatment. In the presence of 10 μM atraric acid, the LNCaP cells exhibited reduced growth while the treatment with OH—F (hydroxyflutamide) did not lead to any reduction in growth. The latter may be due to LNCaP cells having a point mutation in the ligand binding domain of the human androgen receptor that prevents OH—F from acting as an antiandrogen in these cells.

These data show that the androgen antagonism of atraric acid is also effective in the case of a mutated human androgen receptor. Thus, atraric acid is able to inhibit growth of LNCaP cells. Consequently, atraric acid could also be used to treat prostate carcinomas that are resistant to known antiandrogenic active agents such as hydroxyflutamide.

The present invention thus also relates to the use of atraric acid for treating prostate carcinoma and for manufacturing a medicament for treating prostate carcinoma, particularly of prostate carcinomas that are resistant to treatment with known androgen antagonists such as, for example, bicalutamide, flutamide, hydroxyflutamide, nilutamide or cyproterone acetate.

Moreover, atraric acid can serve as a lead substance in the development of novel active substances suitable for treating benign prostatic hyperplasia and/or prostate carcinoma, particularly therapy-resistant prostate carcinoma.

The task underlying the present invention was to provide new antiandrogenic active substances for the treatment of BPH and/or prostate carcinoma or for the production of medicaments used for treating BPH and/or prostate carcinoma.

This task is also solved by providing a number of chemically synthesised derivatives of atraric acid wherein the side chains of the benzene ring or the side chain of the ester have/has been substituted. To optimise the structure of atraric acid, a number of substances were synthesized that differed from atraric acid in their ester group. To this end it was initially attempted to carry out an acid-catalysed esterification of 2,4-dihydroxy-3,5-dimethylbenzoic acid with various primary aliphatic alcohols. As a result of the low carbonyl activity, carboxylic acids generally react only slowly with alcohols. The addition of strong mineral acids, such as sulfuric acid, and refluxing for several hours can considerably increase the reaction speed. However, the reaction of 2,4-dihydroxy-3,5-dimethylbenzoic acid with a primary alcohol, for example ethanol, did not yield the desired ester since at elevated temperatures 2,4-dihydroxy-3,5-dimethylbenzoic acid decarboxylates with mineral acids because of its salicylate structure.

However, an alkali-catalysed reesterification of atraric acid with a primary alcohol yielded the desired ester. To this end, atraric acid was stirred overnight, together with an amount of potassium hydroxide that was somewhat larger than the equimolar amount, in a solution of the corresponding primary aliphatic alcohol or benzene sulfonamide. As this reesterification does not take place quantitatively, the reaction product had to be isolated from the mixture by preparative HPLC.

In this way, the synthesis of the following atraric acid derivatives (atratates), the structural formulas of which are shown in FIG. 5, was successfully carried out:

| | |
|---|---|
| A1= | ethyl-2,4-dihydroxy-3,6-dimethylbenzoate; ethyl atratate |
| A2= | propyl-2,4-dihydroxy-3,6-dimethylbenzoate; propyl atratate |
| A3= | butyl-2,4-dihydroxy-3,6-dimethylbenzoate; butyl atratate |
| A4= | 2-[(phenylsulfonyl)amino]ethyl-2,4-dihydroxy-3,6-dimethylbenzoate |
| A5= | (2E)-3,7-dimethylocta-2,6-dien-1-yl-2,4-dihydroxy-3,5-dimethylbenzoate; geranyl-2,4-dihydroxy-3,5-dimethylbenzoate; geranyl atratate |
| A6= | isopropyl-2,4-dihydroxy-3,5-dimethylbenzoate; isopropyl atratate |

In addition, the following, commercially available compounds, exhibiting a structure similar to that of atraric acid, were examined for their antiandrogenic effect:

| | |
|---|---|
| R0= | ethyl-2,4-dihydroxy-6-methylbenzoate |
| R1= | methyl-3,5-dibromo-2,4-dihydroxy-6-methylbenzoate |
| R2= | methyl-2-hydroxy-3-methylbenzoate |
| R3= | methyl-2,4-dihydroxybenzoate |
| R4= | methyl-2,4-dihydroxy-3-methylbenzoate |
| R5= | methyl-2,6-dihydroxy-3,5-dimethylbenzoate |
| R6= | 2,4-dihydroxy-3,6-dimethylbenzoic acid |
| X= | 1-(2-hydroxy-4,6-dimethoxyphenyl)-ethanone; xanthoxylin. |

Figure 6:
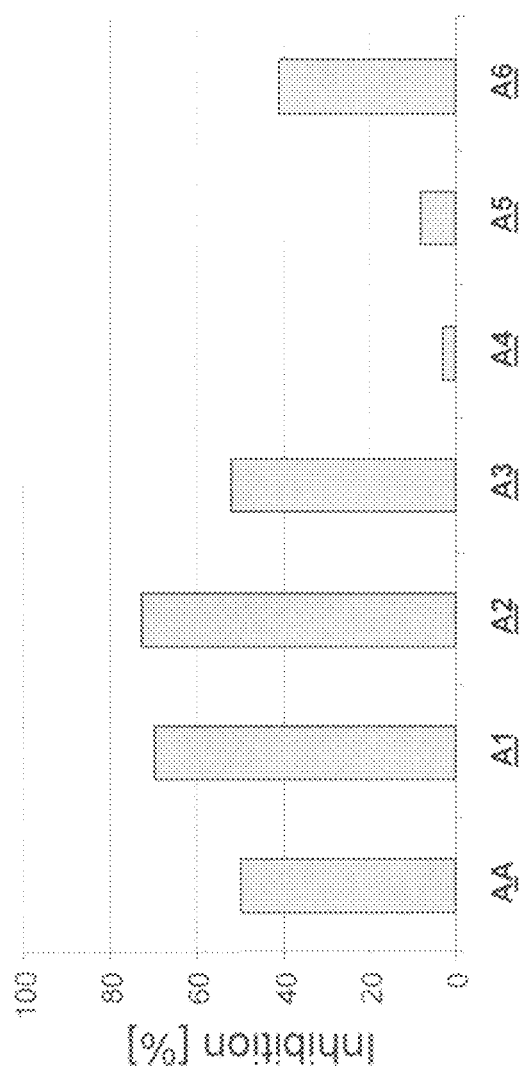
FIG. 6 shows the results of luciferase assays with synthesized structural variants of atraric acid (AA) at a concentration of $10^{-6}$ M.
Figure 7:
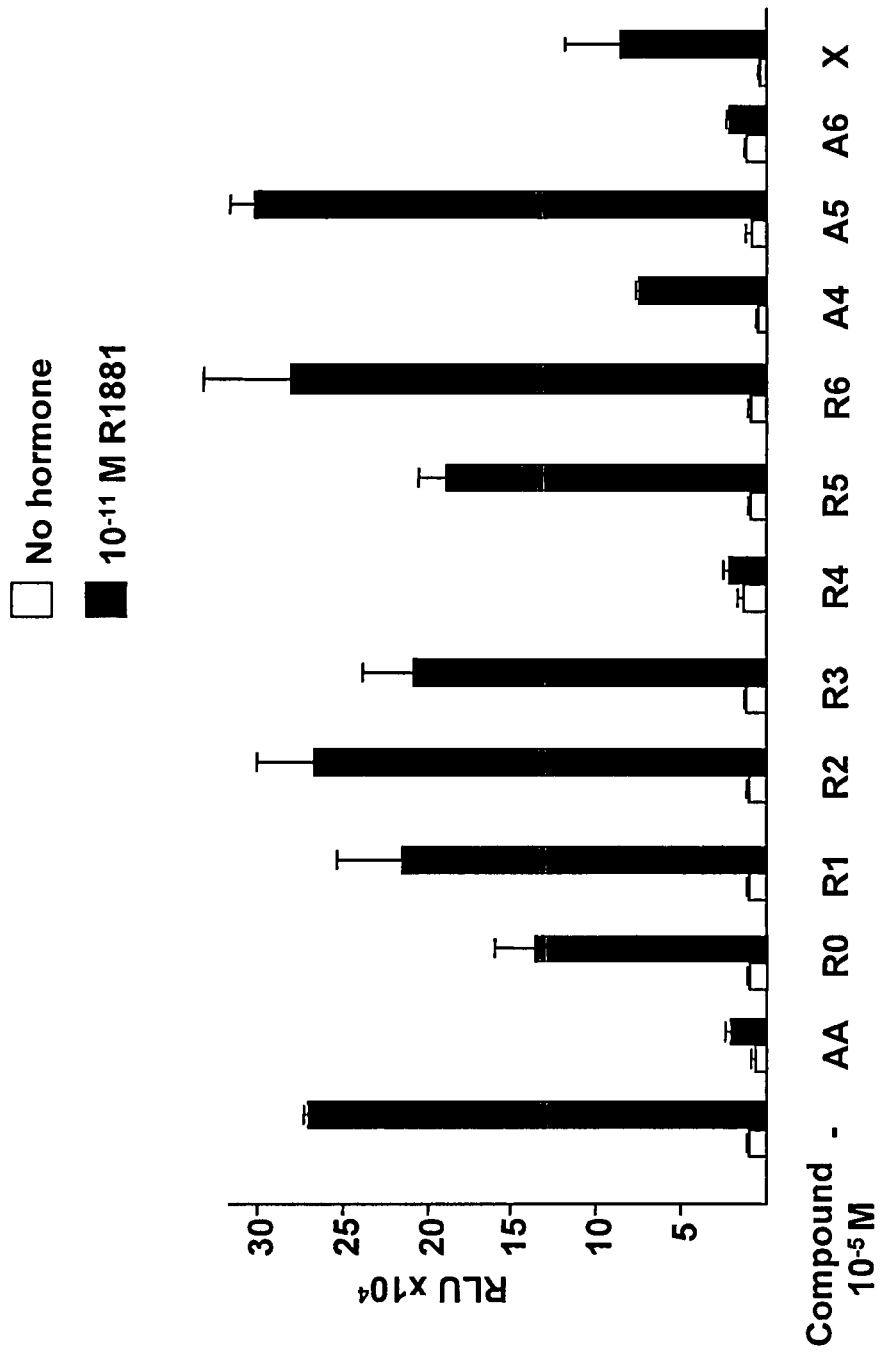
FIG. 7 illustrates the antiandrogenic action of compounds with structural similarities to atraric acid.

The compound A4 is a chimaera of atraric acid and N-butylbenzenesulfonamide but shows no antiandrogenic effect, as is illustrated by FIGS. 6 and 7. This leads to the assumption that in an atraric acid derivative a large side chain as ester does not lead to an antiandrogenically active molecule. This assumption is in accordance with the fact that the replacement of the isopropyl group (compound A) by a larger, more hydrophobic geranyl group (compound A5) did not lead to an antiandrogenically active molecule.

The compounds R4 and A6 showed strong antiandrogenic activity nearly completely inhibiting the androgen receptor-mediated transactivation at 10 μM concentration (FIG. 7). Even at a concentration of only 1 μM both R4 and A6 compounds were still able to inactivate androgen receptor-mediated transactivation.

The results of the luciferase assays suggest that the methyl group at the ortho-position is not required for antiandrogenic activity (as is shown by comparing the effects of atraric acid with those of R4), while a methyl group located at the meta-position is essential for antiandrogenic activity (see activity of R0). In line with that, removing both methyl groups from the benzene ring leads to complete abrogation of anti androgenic activity. Furthermore, the methyl groups cannot be replaced by bromide atoms without leading to the loss of anti androgenic activity, as is revealed by the activity of the compound R1. Also, the compound R5, having all the benzene ring substituents that are found in atraric acid but at different positions, leads to loss of antiandrogenic activity. The methyl group of the ester, too, seems to be essential for antiandrogenic activity since removing it abrogates the antiandrogenic activity, as shown by the activity of R6.

Androgens are indispensable for the normal development, the normal growth and the normal secreting activities of the prostate. By contrast thereto, estrogens are generally considered to be inhibitors of prostate growth. However, such a general assessment of estrogens is likely to be wrong because it could be shown that activation of the ERβ has an inhibiting effect on the growth of prostate cancer cells. Moreover, inactivation of the ER β led to prostate hyperplasia in mice.

Within the framework of the studies made for the present invention, it was also shown that atraric acid does not only have antiandrogenic action, but also acts agonistically on E R β. This finding does not only lead to the assumption that the inhibitory effect of atraric acid on the growth of prostate cancer cells is not due exclusively to its antiandrogenic effect but also to its ER β agonism. Rather, also patients afflicted by other diseases, for example neurodegenerative disorders, could benefit from a treatment with atraric acid or with an atraric acid derivative having an agonistic effect on the ER β.

The subject matter of the invention therefore is the use of a 2,4-dihydroxy-3-methylbenzoate of the general formula

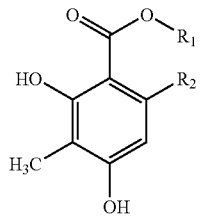

wherein $R_1$ represents a $C_1$ to $C_4$ alkyl, and $R_2$ is hydrogen or a methyl, ethyl or propyl residue, for the treatment and the production of a medicament used for the treatment of benign prostatic hyperplasia and/or prostate carcinoma, especially the prostate carcinoma resistant to androgen antagonist therapy.

The subject matter of the invention is also the use of a 2,4-dihydroxy-3-methylbenzoate of the general formula

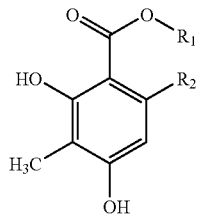

wherein $R_1$ represents a $C_1$ to $C_4$ alkyl, and $R_2$ is hydrogen or a methyl, ethyl or propyl residue, for the treatment and the production of a medicament used for the treatment of spinobulbar muscular atrophy.

The invention further relates to the use of the aforementioned 2,4-dihydroxy-3-methylbenzoate as a lead substance for the development of further or new active substances for treating benign prostatic hyperplasia, prostate carcinoma and spinobulbar muscular atrophy.

The invention further relates to medicaments for the treatment of benign prostatic hyperplasia and/or prostate carcinoma, especially of the prostate carcinoma resistant to a therapy with androgen antagonists, and of spinobulbar muscular atrophy, which medicaments are characterized in that they contain at least one 2,4-dihydroxy-3-methylbenzoate of the general formula

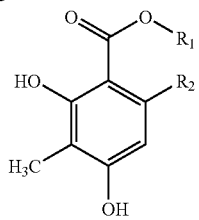

wherein $R_1$ represents a $C_1$ to $C_4$ alkyl, and $R_2$ is hydrogen or a methyl, ethyl or propyl residue.

Furthermore, the invention relates to a process for isolating atraric acid from biological material, comprising the steps of:
a. size reduction of the biological material;
b. extracting the biological material with a solvent selected from the group comprising monovalent $C_1$ to $C_4$ alcohols and readily volatile, (partially) halogenated $C_1$ hydrocarbons;
c. fractionating the extracts; and
d. isolating atraric acid from the fractions containing atraric acid.

The biological material may be the bark of the African plum tree *P. africana* or lichens viable on the bark of *P. africana*. Preferably, the extraction is performed as selective extraction by using a series of successive solvents of increasing polarity, and the fractionation of the extract is performed by gradient extrography, with increasing polarity of the eluent. With particular preference, the isolation of atraric acid from the atraric acid-containing fractions is performed by preparative HPLC.

A further subject matter of the invention is a process for synthesizing atraric acid derivatives (atratates) which is characterised by stirring atraric acid together with an equimolar amount of alkali hydroxide or alkaline earth hydroxide in a solution of a primary aliphatic alcohol, which leads only to reesterification, and by subsequent isolation of the atraric acid derivative from the reaction mixture, preferably by preparative HPLC.

Preferably, the alkali hydroxide used is potassium hydroxide, and with particular preference the primary aliphatic alcohol is selected with particular preference from the group comprising methanol, ethanol, n-propanol, iso-propanol and butanol.

A further subject matter of the invention are atraric acid derivatives comprising a 2,4-dihydroxybenzoate of the general formula

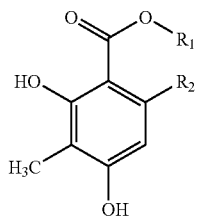

wherein $R_2$ is hydrogen or a methyl, ethyl or propyl residue, which are characterized in that $R_1$ is selected from the group comprising an iso-propyl, geranyl and ethylbenzenesulfonamide residue.

EXAMPLE 1

Extraction of the Plant Material

Dried bark of the African plum tree (*P. africana*) was powdered, and 1.73 kg of the powdered bark was homogenized in 1 l n-hexane, with ice-cooling, using an ULTRA TURRAX®. The plant material was filled into a column (Merck PREPBAR® 400×100 mm) and selectively extracted successively with 25.0 l of n-hexane, 26.0 l of methylene chloride, 25.0 l of methanol (MeOH) and 12.5 l of water at room temperature. The solvents of the resulting extracts were evaporated in vacuo at 40° C. This yielded 4.8 g selective hexane extract, 11.03 g selective methylene chloride extract, 116.81 g selective methanol extract and 7.00 g selective water extract.

For preparing an ethanolic extract, 300 g bark material of *P. africana* was powdered and extracted three times, each time with 5.0 l ethanol (EOH). After filtering the extract through filter paper of 0.7 µm pore size, the solvent was removed from the entire extract at 40° C. using a rotary evaporator. The dry matter of the resulting extract was 16.02 g.

EXAMPLE 2

Fractionation of the Methylene Chloride Extract

The selective methylene chloride extract of *Pygeum africana* was fractionated with silica gel (Macherey-Nagel Si60, 15-25 µm). For this purpose the extract was dissolved in 2000 ml $CH_2Cl_2$ and filtered through filter paper with a pore size of 0.7 µm (Schleicher & Schüll). 25 g of silica gel (Merck Si60, 0.063-0.2 mm) was added to the extract and the solvent was then evaporated in vacuo at 40° C. The thus-coated silica gel was placed on top of a dry packed silica gel column (Merck PREPBAR® 400×100 mm) and eluted, at a flow rate of 120 ml·min$^{-1}$, with a linear gradient of 0 min hexane (100:0), 50 min hexane (100:0), 350 min $CH_2Cl_2$ (100:0), 500 min $CH_2Cl_2$ (100:0), 700 min $CH_2Cl_2$-MeOH (80:20), 750 min MeOH (100:0), 800 min MeOH (100:0), 850 min $H_2O$ (100:0), 885 min $H_2O$. The chromatography gave 35 fractions which led to detection by UV light at a wavelength of 245 nm (Table 1).

TABLE 1

Fractionation of the selective methylene chloride extract from *P. africana*

| Fraction | Min | Mass (mg) |
|---|---|---|
| F1 | 0-148 | 3 |
| F2 | 149-184 | 52 |
| F3 | 185-204 | 33 |
| F4 | 205-229 | 63 |
| F5 | 230-238 | 14 |
| F6 | 239-261 | 61 |
| F7 | 262-266 | 30 |
| F8 | 267-293 | 243 |
| F9 | 294-331 | 380 |
| F10 | 332-338 | 17 |
| F11 | 339-356 | 164 |
| F12 | 357-369 | 119 |
| F13 | 370-373 | 38 |
| F14 | 374-375 | 71 |

TABLE 1-continued

Fractionation of the selective methylene chloride extract from P. africana

| Fraction | Min | Mass (mg) |
|---|---|---|
| F15 | 376-562 | 110 |
| F16 | 563-581 | 44 |
| F17 | 582-592 | 24 |
| F18 | 593-614 | 1537 |
| F19 | 615-630 | 799 |
| F20 | 631-638 | 292 |
| F21 | 639-659 | 1338 |
| F22 | 660-663 | 20 |
| F23 | 664-671 | 327 |
| F24 | 672-692 | 634 |
| F25 | 693-703 | 157 |
| F26 | 704-724 | 333 |
| F27 | 725-749 | 350 |
| F28 | 750-771 | 393 |
| F29 | 772-784 | 316 |
| F30 | 785-803 | 141 |
| F31 | 804-820 | 57 |
| F32 | 821-828 | 58 |
| F33 | 829-836 | 1 |
| F34 | 837-858 | 126 |
| F35 | 859-880 | 1 |

EXAMPLE 3

Isolation of Atraric Acid

Atraric acid was isolated from fraction F8 by preparative HPLC (250×21 mm, 100-5 C18 HD Macherey-Nagel, 22 ml·min$^{-1}$, UV detection at 220 mm, Gradient: 0 min ACN—H$_2$O (with addition of 0.1% of TFA) ((20:80), 40 min ACN—H$_2$O (80:20), 45 min ACN (acetonitrile) (100:0)). Atraric acid was collected from minute 23 to minute 25. Its structure was elucidated on the basis of the $^1$H NMR and $^{13}$C NMR, EI-MS, HR-EI-MS, IR and UV spectra.

EXAMPLE 4

Cell Culture and Luciferase Assay

Monkey kidney cells, line CV1, lacking endogenous androgen receptor, were cultured in Dulbecco's modified Eagle's medium (DMEM), supplemented with 10% (v/v) fetal calf serum, penicillin (100 IU/ml) and streptomycin (100 IU/ml), at 37° C. and 5% CO$_2$.

For the transfection experiments, the cells were seeded onto 6-well cell culture plates (Nunc, Roskilde, Denmark) with a density of 1.2×10$^5$ cells per well, and grown in DMEM medium supplemented with 10% (v/v) dextran-coated activated charcoal stripped serum. Six hours after seeding, the cells were transfected by using the Ca$_3$(PO$_4$)$_2$ method. The human androgen receptor (hAR) expression vector (0.2 µg) was cotransfected with 1 µg of the reporter plasmid MMTV-luc and 0.2 µg of the cytomegalovirus (CMV)-driven β-galactosidase expression virus, as internal control for transfection efficiency. After 14 hours, the medium was replaced either without (white bars in FIGS. 1 to 3) or with the addition of methyltrienolone (R1881, 3×10$^{-10}$ M final concentration; black bars in FIGS. 1 to 3) together with the indicated extracts (FIG. 1), fractions of the methylene chloride extract (FIG. 2) or individual isolated compounds (FIG. 3). After an additional 48 hours, cells were harvested and assayed for luciferase and β-galactosidase activity.

Luciferase activity was determined by injecting luciferin and measuring light emission at 562 nm and expressed as relative light units (RLU) by using the values of β-galactosidase activity for normalisation of the luciferase activity. All transfection assays shown were performed in duplicate and were repeated at least twice.

For determining antiandrogenic activity in the various extracts from the bark of P. africana, the extracts were used at a concentration of 300 µg/ml. The results are shown in FIG. 1.

Figure 2:
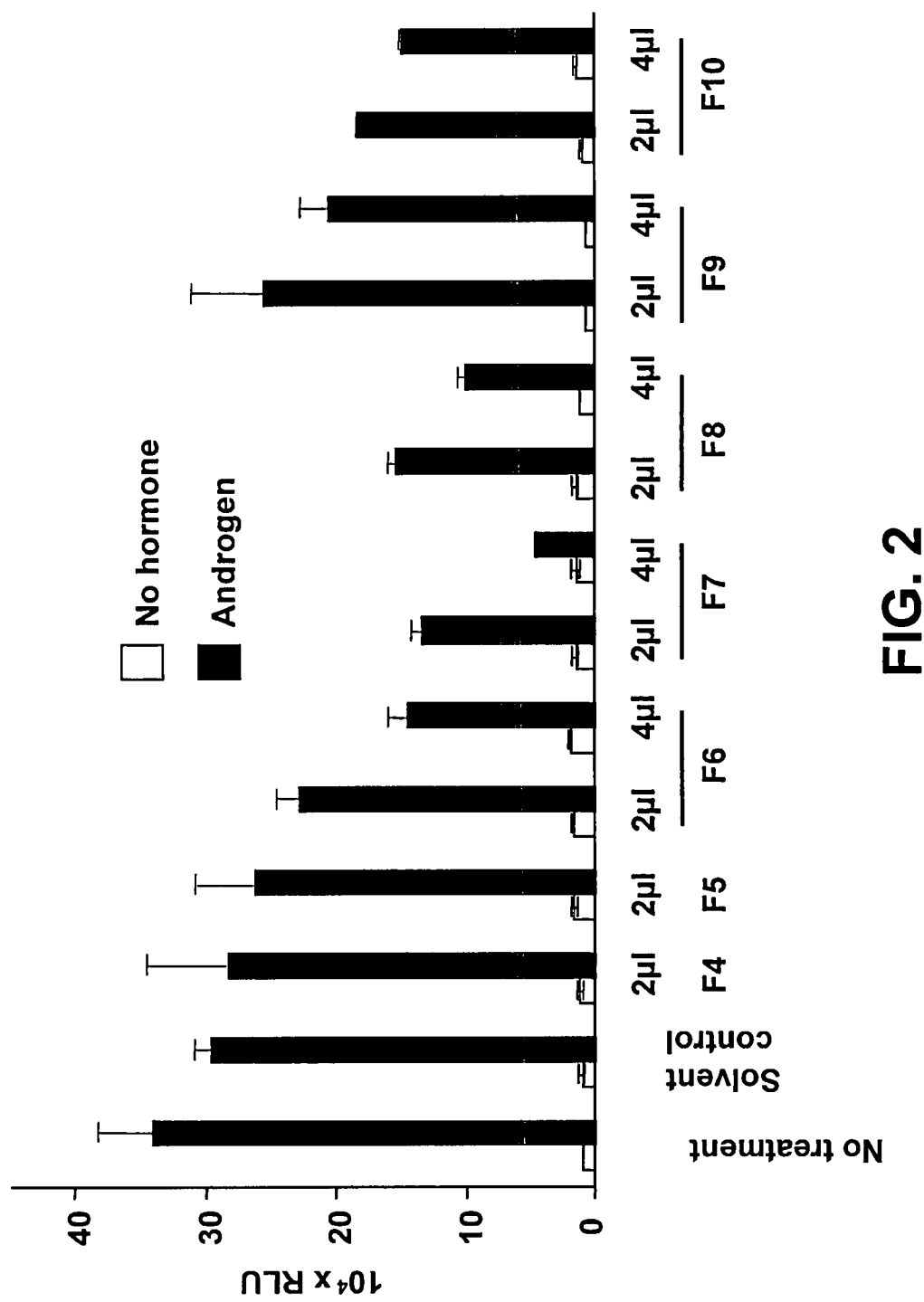
FIG. 2 shows the antiandrogenic action of fractions of a selective methylene chloride extract from *P. africana*.

For determining the antiandrogenic activity in the fractions of the selective methylene chloride extracts, 2 µl of the respective fraction was used, corresponding to a final concentration of 30 µg/ml. Fractions 6 to F10 were additionally tested with 4 µl, corresponding to 60 µg/ml final concentration. Active fractions F7 and F8 were used for the further tests. Part of the results is shown in FIG. 2.

Inhibition of the substances isolated from fraction F8 of the selective methylene chloride extract is represented in FIG. 3 as the percent inhibition of androgen activity. The substances were each used at a concentration of 30 µg/ml.

EXAMPLE 5

Growth Inhibition of Human Prostate Carcinoma Cells by Atraric Acid

Human prostate carcinoma cells (cell line LNCaP) were cultured in RPMI-1640 medium that was supplemented with 10% (v/v) fetal calf serum, penicillin (100 IU/ml) and streptomycin (100 IU/ml), 2 mM glutamine and 1 mM sodium pyruvate.

For the cell growth assays, LNCaP cells were seeded onto a 24-well cell culture plate at a density of 5×10$^3$ cells per well and cultured in RPMI-1640 medium containing 5% fetal calf serum. On day 2, the culture medium was replaced, and ethanol/DMSO (control), atraric acid (1 µM and 10 µM) or the known antiandrogen hydroxyflutamide (OH—F) (0.1 µM) was added to treat the cells. Every second day the medium was replaced with fresh medium together with freshly added compounds. The cells were trypsinized and counted using a counting cell chamber on the indicated days. The results are shown in FIG. 5.

EXAMPLE 6

Synthesis of Methylbenzene Sulfonamide (=S1)

Empirical formula: C$_{11}$H$_{14}$O$_4$ (MW=210.09)
IUPAC: Ethyl-2,4-dihydroxy-3,6-dimethylbenzoate
Appearance: white powder
Synthesis:

392 mg atraric acid (2 mmol) were stirred with 118 mg potassium hydroxide (2.1 mmol) in 10 ml ethanol overnight and then neutralised. The solvent was withdrawn in the rotary evaporator and the residue dissolved in the solvent mixture of the chromatographic starting conditions. Subsequently, the reaction product was isolated by preparative HPLC according to method B4:

| B4 | Macherey - Nagel NUCLEOSIL ® 100-5-C-18HD, 5 µm, 250 × 21 mm | A: Acetonitrile/0.1% TFA B: Water/0.1% TFA Isocratic: 50% A, 50% B | 22.0 ml/min | PDA: λ = 220 nm |
|---|---|---|---|---|

Retention time 13 min
Yield: 42 mg (10%)
Melting point: (° C.): 127

UV (MeOH) $\lambda_{max}$ nm: 217, 265, 308
IR (KBr) $v_{max}$ cm$^{-1}$: 3450, 3100, 1620, 1310, 1280, 800
$^1$H-NMR (500 MHz, CDCl$_3$), δ (ppm):
12.05 (1H, s, C-2-OH)
6.14 (1H, s, C-5-H)
5.02 (1H, s, C-4-OH)
4.32 (2H, q, $^3$J=7.0 Hz, C-1'-H)
2.41 (3H, s, C-6-Me)
2.03 (3H, s, C-3-Me)
1.34 (3H, t, $^3$J=7.0 Hz, C-2'-H)
$^{13}$C-NMR (125 MHz, CDCl$_3$), δ (ppm):

| 172.1 (C-7) | 108.5 (C-3) | 7.6 (C-3-Me) |
| 163.2 (C-2) | 105.4 (C-1) | |
| 157.9 (C-4) | 61.2 (C-1') | |
| 140.2 (C-6) | 24.6 (C-6-Me) | |
| 110.5 (C-5) | 14.2 (C-2') | |

EI-MS (70 eV): m/z (rel. int.):
210 [M]$^+$ (50), 164 (100), 136 (60)
High-accuracy mass determination (HR-EI-MS):
Calculated: 210.0892 for [M$^+$]
Found: 210.0889

EXAMPLE 7

Synthesis of Propyl Atratate (A2)

Empirical formula: C$_{12}$H$_{16}$O$_4$ (MW=224.10)
IUPAC: Propyl-2,4-dihydroxy-3,6-dimethylbenzoate
Appearance: white powder
Synthesis:
392 mg atraric acid (2) (2 mmol) was stirred with 118 mg potassium hydroxide (2.1 mmol) in 10 ml propanol overnight and then neutralised. The solvent was withdrawn in the rotary evaporator and the residue dissolved in the solvent mixture of the chromatographic starting conditions. Subsequently, the reaction product was isolated by preparative HPLC according to method B5:

| B5 | Macherey - Nagel NUCLEOSIL ® 100-5-C-18HD, 5 μm, 250 × 21 mm | A: Methanol B: Water/0.1% TFA Isocratic: 72% A, 28% B | 22.0 ml/min | PDA: λ = 220 nm |

Retention time: 10 Min.
Yield: 31 mg (7%)
Melting point (° C.): 134
UV (MeOH) $\lambda_{max}$ nm: 217, 262, 307
IR (KBr) $v_{max}$ cm$^{-1}$: 3450, 3000, 1650, 1310, 1200, 800
$^1$H-NMR (500 MHz, CDCl$_3$), δ (Ppm):
12.09 (1H, s, C-2-OH)
6.14 (1H, s, C-5-H)
5.02 (1H, s, C-4-OH)
4.23 (2H, t, $^3$J=6.7 Hz, C-1'-H)
2.41 (3H, s, C-6-Me)
2.04 (3H, s, C-3-Me)
1.73 (2H, m, $^3$J=7.0 Hz, C-2'-H)
0.97 (3H, t, $^3$J=7.2 Hz, C-3'-H)
$^{13}$C-NMR (125 MHz, CDCl$_3$), δ (ppm):

| 173.3 (C-7) | 108.5 (C-3) | 10.8 (C-3') |
| 163.2 (C-2) | 105.4 (C-1) | 7.6 (C-3-Me) |
| 157.9 (C-4) | 67.0 (C-1') | |
| 140.1 (C-6) | 24.2 (C-6-Me) | |
| 110.5 (C-5) | 22.0 (C-2') | |

EI-MS (70 eV): m/z (rel. int.):
224 [M]$^+$ (31), 164 (100), 136 (44)
High-accuracy mass determination (HR-EI-MS):
Calculated: 224.1049 for [M$^+$]
Found: 224.1051

EXAMPLE 8

Synthesis of Butyl Atratate (A3)

Empirical formula: C$_{13}$H$_{18}$O$_4$ (MW=238.12)
IUPAC: Butyl-2,4-dihydroxy-3,6-dimethylbenzoate
Appearance: white powder
Synthesis:
392 mg atraric acid (2) (2 mmol) was stirred with 118 mg potassium hydroxide (2.1 mmol) in 10 ml butanol overnight and then neutralised. The solvent was withdrawn in the rotary evaporator and the residue dissolved in the solvent mixture of the chromatographic starting conditions. Subsequently, the reaction product was isolated by preparative HPLC according to method B7:

| B7 | Macherey - Nagel NUCLEOSIL ® 100-5-C-18HD, 5 μm, 250 × 21 mm | A: Methanol B: Water/0.1% TFA | 22.0 ml/min | PDA: λ = 220 nm |
| | | Time [min] | A [%] | B [%] |
| | | 0 | 75 | 25 |
| | | 20 | 75 | 25 |
| | | 25 | 100 | 0 |

Retention time 13 Min.
Yield: 51 mg (11%)
Melting point (° C.): 117
UV (MeOH) $\lambda_{max}$ nm: 217, 265, 308
IR (KBr) $v_{max}$ cm$^{-1}$: 3440, 3000, 1700, 1310, 1200, 800
$^1$H-NMR (500 MHz, CDCl$_3$), δ (ppm):
12.09 (1H, s, C-2-OH)
6.20 (1H, s, C-5-H)
4.97 (1H, s, C-4-OH)
4.32 (2H, t, $^3$J=7.0 Hz, C-1'-H)
2.41 (3H, s, C-6-Me)
2.04 (3H, s, C-3-Me)
1.69 (2H, m, $^3$J=7.3 Hz, C-2'-H)
1.42 (2H, m, $^3$J=7.3 Hz, C-3'-H)
0.90 (3H, t, $^3$J=7.3 Hz, C-4'-H)
$^{13}$C-NMR (125 MHz, CDCl$_3$), δ (ppm):

| 167.9 (C-7) | 108.6 (C-3) | 19.3 (C-3') |
| 163.1 (C-2) | 105.5 (C-1) | 13.5 (C-4') |
| 157.8 (C-4) | 66.3 (C-1') | 7.5 (C-3-Me) |
| 140.1 (C-6) | 24.1 (C-6-Me) | |
| 110.5 (C-5) | 30.5 (C-2') | |

EI-MS (70 eV): m/z (rel. int.):
238 [M]$^+$ (31), 164 (100), 136 (30)

High-accuracy mass determination (HR-EI-MS):
Calculated: 238.1226 for [M$^+$]
Found: 238.1226

EXAMPLE 9

Synthesis of a Hybrid of Atraric Acid and N-butylbenzenesulfonamide (A4)

Empirical formula: $C_{17}H_{19}O_6NS$ (MW=365.09)
IUPAC: 2-[(Phenylsulfonyl)amino]ethyl 2,4-dihydroxy-3,6-dimethylbenzoate
Appearance: yellowish powder
Synthesis:
1.822 g of 2,4-dihydroxy-3,6-dimethylbenzoic acid (0.01 mol) and 3.522 g N-(2-hydroxyethyl)benzenesulfonamide were treated under reflux for 5 hours in 30 ml ortho-toluene with addition of 0.05 g sulfuric acid conc. After neutralisation, the solvent was withdrawn at the rotary evaporator, and the residue was dissolved in the solvent mixture of the chromatographic starting conditions. Subsequently, the reaction product was isolated by preparative HPLC according to method B9:

| B9 | Macherey - Nagel NUCLEOSIL ® 100-5-C-18HD, 5 μm, 250 × 21 mm | A: Methanol B: Water/0.1% TFA Isocratic: 60% A, 40% B | 22.0 ml/min | PDA: λ = 220 nm |
|---|---|---|---|---|

Retention time 14 min
Yield: 30 mg (4%)
Melting point (° C.): 151
UV (MeOH) $\lambda_{max}$ nm: 220, 270, 305
IR (KBr) $v_{max}$ cm$^{-1}$: 3450, 3310, 2930, 1640, 1310, 1280, 1160, 1100
$^1$H-NMR (500 MHz, CDCl$_3$), δ (ppm):
11.69 (1H, s, C-2-OH)
7.79 (2H, d, $^3$J=7.0 Hz, C-2"-H und C-6"-H)
7.48 (1H, t, $^3$J=7.0 Hz, C-4"-H)
7.41 (2H, t, $^3$J=7.0 Hz, C-3"-H und C-5"-H)
6.13 (1H, s, C-5-H)
5.05 (1H, s, C-4-OH)
4.68 (1H, s, N—H)
4.31 (2H, t, $^3$J=5.5 Hz, C-1'-H)
3.32 (2H, t, J=5.5 Hz, C-2'-H)
2.31 (3H, s, C-6-Me)
2.03 (3H, s, C-3-Me)
$^{13}$C-NMR (125 MHz, CDCl$_3$), δ (ppm):

| 167.0 (C-7) | 133.6 (C-4") | 104.2 (C-1) |
|---|---|---|
| 163.0 (C-2) | 130.2 (C-3" and C-5") | 64.5 (C-1') |
| 153.1 (C-4) | 127.8 (C-2" and C-6") | 43.0 (C-2') |
| 142.0 (C-6) | 111.6 (C-5) | 24.6 (C-6-Me) |
| 141.4 (C-1") | 109.9 (C-3) | 7.5 (C-3-Me) |

EI-MS (70 eV): m/z (rel. int.):
365 [M]$^+$ (23), 170 (26), 164 (100), 141 (26), 136 (24), 77 (27)
High-accuracy mass determination (HR-EI-MS):
Calculated: 365.0933 for [M$^+$]
Found: 365.0933

EXAMPLE 10

Synthesis of Geranyl Atratate (A5)

Empirical formula: $C_{19}H_{26}O_4$ (MW=318.18)
IUPAC: (2E)-3,7-Dimethylocta-2,6-diene-1-yl 2,4-dihydroxy-3,6-dimethylbenzoate
Appearance: yellowish powder
Synthesis:
392 mg atraric acid (2) (2 mmol) was stirred overnight with 118 mg potassium hydroxide (2.1 mmol) in 10 ml geraniol and then neutralised. The solvent was withdrawn in the rotary evaporator and the residue dissolved in the solvent mixture of the chromatographic starting conditions. Subsequently, the reaction product was isolated by preparative HPLC according to method B8:

| B8 | Macherey - Nagel NUCLEOSIL ® 100-5-C-18HD, 5 μm, 250 × 21 mm | A: Acetonitrile/0.1% TFA B: Water/0.1% TFA Isocratic: 50% A, 50% B | 22.0 ml/min | PDA: λ = 220 nm |
|---|---|---|---|---|

Retention time 27 Min.
Yield: 44 mg (7%)
UV (ACN) $\lambda_{max}$ nm: 220, 270, 310
IR (KBr) $v_{max}$ cm$^{-1}$: 3410, 2930, 1640, 1440, 1270
$^1$H-NMR (500 MHz, MeOH-d4), δ (ppm):
6.20 (1H, s, C-5-H)
2.45 (3H, s, C-6-Me)
5.34 (1H, t, $^3$J=6.7 Hz, C-2'-H)
5.10 (1H, t, $^3$J=6.7 Hz, C-6'-H)
4.07 (2H, d, $^3$J=6.5 Hz, C-1'-H)
2.10 (2H, q, $^3$J=8.3 Hz, C-5'-H)
2.01 (2H, t, $^3$J=8.3 Hz, C-4'-H)
1.99 (3H, s, C-3 Me)
1.65 (3H, s, C-3'-Me)
1.64 (3H, s, C-7'-Me)
1.59 (3H, s, C-8')
$^{13}$C-NMR (125 MHz, MeOH-d4), δ (ppm):

| 175.6 (C-7) | 132.4 (C-7') | 104.9 (C-1) | 24.3 (C-6-Me) |
|---|---|---|---|
| 164.8 (C-2) | 125.1 (C-2') | 59.4 (C-1') | 17.7 (C-5') |
| 161.3 (C-4) | 124.9 (C-6') | 40.7 (C-4') | 16.2 (C-3'-Me) |
| 141.5 (C-3') | 111.3 (C-5) | 27.5 (C-8') | 7.9 (C-3-Me) |
| 139.4 (C-6) | 109.7 (C-3) | 25.8 (C-7'-Me) | |

EI-MS (70 eV): m/z (rel. int.):
318 [M]$^+$ (24), 164 (100), 136 (38)
High-accuracy mass determination (HR-EI-MS):
Calculated: 318.1834 for [M$^+$]
Found: 318.1829

EXAMPLE 11

Synthesis of Isopropyl Atratate (A6)

Empirical formula: $C_{12}H_{16}O_4$ (MW=224.10)
IUPAC: Isopropyl-2,4-dihydroxy-3,6-dimethylbenzoate
Appearance: white powder
Synthesis:
392 mg atraric acid (2) (2 mmol) was stirred with 118 mg potassium hydroxide (2.1 mmol) in 10 ml iso-propanol overnight and then neutralised. The solvent was withdrawn in the rotary evaporator and the residue dissolved in the solvent mixture of the chromatographic starting conditions. Subsequently, the reaction product was isolated by preparative HPLC according to method B6:

| B6 | Macherey - Nagel NUCLEOSIL® 100-5-C-18HD, 5 μm, 250 × 21 mm | A: Methanol B: Water/0.1% TFA Isocratic: 70% A, 30% B | 22.0 ml/min | PDA: $\lambda = 220$ nm |
|---|---|---|---|---|

Retention time 12 Min.
Yield: 38 mg (8%)
Melting point (° C.): 90
UV (MeOH) $\lambda_{max}$ nm: 217, 265, 300
IR (KBr) $v_{max}$ cm$^{-1}$: 3400, 3000, 1650, 1310, 1200, 800
$^1$H-NMR (500 MHz, CDCl$_3$), δ (ppm):
12.11 (1H, s, C-2-OH)
6.13 (1H, s, C-5-H)
5.22 (1H, m, $^3$J=6.3 Hz, C-1'-H)
2.40 (3H, s, C-6-Me)
2.03 (3H, s, C-3-Me)
1.31 (6H, d, $^3$J=6.2 Hz, C-1'-Me)
$^{13}$C-NMR (125 MHz, CDCl$_3$), δ (ppm):

| 171.6 (C-7) | 108.5 (C-3) | 7.6 (C-3-Me) |
|---|---|---|
| 163.2 (C-2) | 105.7 (C-1) | |
| 157.8 (C-4) | 69.2 (C-1') | |
| 140.1 (C-6) | 24.3 (C-6-Me) | |
| 110.4 (C-5) | 22.0 (C-1'-Me) | |

EI-MS (70 eV): m/z (rel. int.):
224 [M]$^+$ (35), 164 (100), 136 (39)
High-accuracy mass determination (HR-EI-MS):
Calculated: 224.1049 for [M$^+$]
Found: 224.1051

EXAMPLE 12

Atraric Acid as Agonist for Estrogen Receptors

CV1 cells exhibiting no significant amounts of a functional estrogen receptor were cotransfected, for functional assays with an expression plasmid which encodes the gene for luciferase as reporter gene (p2ERE-TATA-luc) and with an expression plasmid which encodes the human ERβ or the human ERα For the transient transfection experiments with the estrogen receptors, phenol red-free DMEM medium (invitrogen) was supplemented with 10% (v/v) serum which had previously been purified with dextran-coated charcoal, 1% (v/v) glutamine, 1% (v/v) sodium pyruvate and 1% (v/v) penicillin streptomycin. After seven days, the cells were seeded in 6-well plates (Nunc, Roskilde, Denmark) at a density of 1.5×10$^5$ cells per well. After 24 hours, the cells were transfected according to the calcium phosphate method with 2 μg of the reporter gene-encoding expression plasmid, 0.2 μg of the ERα-encoding or ERβ-encoding expression plasmid and, for reasons of normalisation, 0.2 μg of the cytomegalovirus-derived β-galactosidase. After 14 hours, the culture medium was replaced by fresh medium, with or without estradiol but in any case with a corresponding amount of atraric acid added thereto. After 48 hours, the cells were harvested and assayed for luciferase and β-galactosidase activity. All transfection assays were performed in duplicate and were repeated at least twice.

Figure 8:
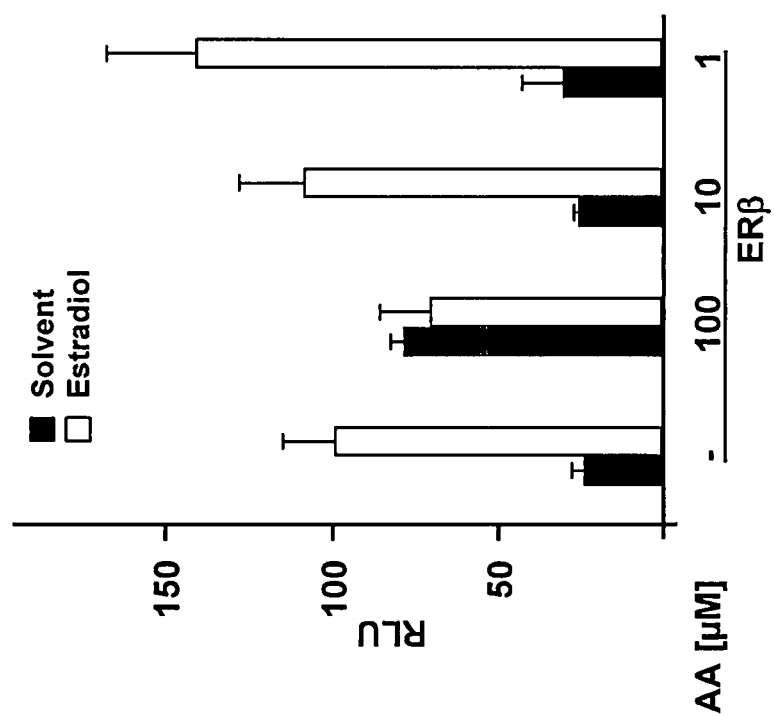
FIG. 8 illustrates the agonistic effect of atraric acid on the estrogen receptor beta.
Figure 9:
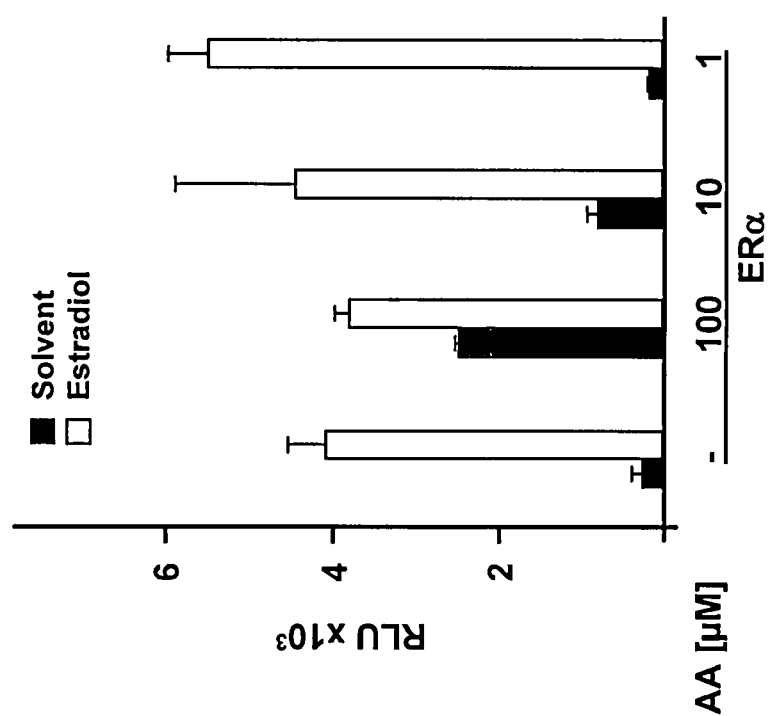
FIG. 9 illustrates the agonistic effect of atraric acid on the estrogen receptor alpha.

The results are graphically represented in FIGS. 8 and 9. These experimental results show that the activity of the two estrogen receptors is influenced by atraric acid. Surprisingly, the hormone-mediated transactivation of the two estrogen receptors was not affected by atraric acid. If no estradiol was present, however, estrogen-responsive expression of the reporter gene was activated in a dose-dependent manner by the presence of 10 μM or 100 μM as is evident from the measured luciferase activity. Thus, at higher concentrations atraric acid is an agonist of both estrogen receptors.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A method for treating prostate carcinoma in a subject, comprising the step of administering an isolated 2,4-dihydroxy-3-methylbenzoate of the general formula

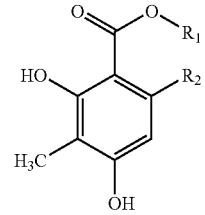

to the subject in an amount in the range of about 1 μmol/L-100 μmol/L, wherein R$_1$ represents a C$_1$ to C$_4$ alkyl, and R$_2$ is selected from the group consisting of hydrogen, a methyl residue, an ethyl residue and a propyl residue.

2. The method according to claim 1, wherein the prostate carcinoma is therapy-resistant to androgen antagonists.

3. The method according to claim 2, wherein the androgen antagonist is selected from the group consisting of bicalutamide, flutamide, hydroxyflutamide, nilutamide and cyproterone acetate.

4. The method according to claim 1,
wherein R$_2$ is hydrogen and R$_1$ is selected from the group consisting of an iso-propyl residue, a geranyl residue and an ethylbenzenesulfonamide residue, or
R$_2$ is a methyl residue and R$_1$ is selected from the group consisting of a geranyl residue and an ethylbenzenesulfonamide residue, or
R$_2$ is an ethyl residue and R$_1$ is selected from the group consisting of an iso-propyl residue, a geranyl residue and an ethylbenzenesulfonamide residue, or
R$_2$ is a propyl residue and R$_1$ is selected from the group consisting of an iso-propyl residue, a geranyl residue and an ethylbenzenesulfonamide residue.

5. A process for isolating atraric acid from biological material, comprising the steps of:
reducing the size of the biological material; selectively extracting the biological material by a series of successive solvents of increasing polarity to form an extract, said solvents being selected from the group consisting of monovalent C$_1$ to C$_4$ alcohols and readily volatile, (partially) halogenated C$_1$ hydrocarbons;

fractionating the extract to form fractions containing atraric acid, said step of fractionating the extract comprising using gradient extrography with increasing polarity of the eluents; and isolating the atraric acid from the fractions containing atraric acid by preparative HPLC, wherein said biological material is selected from the group consisting of the bark of the African plum tree *P. africana* and lichens viable on the bark of *P. africana*.

6. The method according to claim 1, wherein $R_1$ is methyl and $R_2$ is methyl.

7. A method for treating prostate carcinoma in a subject, comprising the step of administering a synthetic compound of the general formula

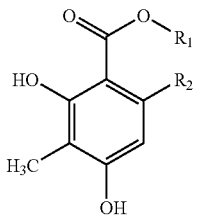

to the subject in an amount in the range of about 1 μmol/L-100 μmol/L, wherein $R_1$ represents a $C_1$ to $C_4$ alkyl, and $R_2$ is selected from the group consisting of hydrogen, a methyl residue, an ethyl residue and a propyl residue.

8. The method according to claim 7, wherein the prostate carcinoma is therapy-resistant to androgen antagonists.

9. The method according to claim 8, wherein the androgen antagonist is selected from the group consisting of bicalutamide, flutamide, hydroxyflutamide, nilutamide and cyproterone acetate.

10. The method according to claim 1,
wherein $R_2$ is hydrogen and $R_1$ is selected from the group consisting of an iso-propyl residue, a geranyl residue and an ethylbenzenesulfonamide residue, or $R_2$ is a methyl residue and $R_1$ is selected from the group consisting of a geranyl residue and an ethylbenzenesulfonamide residue, or $R_2$ is an ethyl residue and $R_1$ is selected from the group consisting of an iso- propyl residue, a geranyl residue and an ethylbenzenesulfonamide residue, or $R_2$ is a propyl residue and $R_1$ is selected from the group consisting of an iso-propyl residue, a geranyl residue and an ethylbenzenesulfonamide residue.

11. The method according to claim 7, wherein $R_1$ is methyl and $R_2$ is methyl.

12. A method for treating prostate carcinoma in a subject, comprising the step of administering an isolated 2,4-dihydroxy-3-methylbenzoate of the general formula

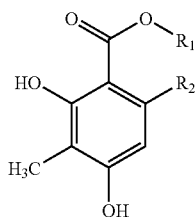

to the subject in a concentration in the range of about 1 μM-100 μM or about 30 μg/ml-60 μg/ml, wherein $R_1$ represents a $C_1$ to $C_4$ alkyl, and $R_2$ is selected from the group consisting of hydrogen, a methyl residue, an ethyl residue and a propyl residue.

* * * * *